United States Patent [19]

Brunsting

[11] 4,115,011

[45] Sep. 19, 1978

[54] CUVETTE CONFIGURED FOR PHOTOANALYSIS USE

[75] Inventor: Albert Brunsting, Miramar, Fla.

[73] Assignee: Coulter Electronics, Inc., Hialeah, Fla.

[21] Appl. No.: 730,577

[22] Filed: Oct. 7, 1976

[51] Int. Cl.² .................................................. G01N 1/10
[52] U.S. Cl. ..................................... 356/246; 250/576
[58] Field of Search ............... 356/246, 201, 180, 184; 250/576

[56] References Cited

U.S. PATENT DOCUMENTS

| | | | |
|---|---|---|---|
| 2,649,011 | 8/1953 | Black | 356/246 |
| 3,535,023 | 10/1970 | Yamanaka et al. | 356/246 |
| 3,700,338 | 10/1972 | Trundle | 356/246 |

*Primary Examiner*—Vincent P. McGraw
*Attorney, Agent, or Firm*—Silverman, Cass & Singer, Ltd.

[57] ABSTRACT

A cuvette for containing a fluid to be analyzed by a single or multiple passage therethrough of a light beam whose rays are substantially parallel to each other. The cuvette is configured such that the substantially parallel light rays incident onto the cuvette remain substantially parallel after one or more passages of the light rays through the cuvette or the light rays have a minimum beam diameter at a selected distance from the cuvette. This is accomplished while the cuvette has a fluid holding configuration that minimizes contamination of subsequent sample placed therein.

15 Claims, 12 Drawing Figures

CUVETTE CONFIGURED FOR PHOTOANALYSIS USE

BACKGROUND OF THE INVENTION

This invention relates to cuvettes for use in photoanalysis apparatus and more particularly, to specially configured cuvettes for use in such apparatus.

Many different types of tests are performed by photoanalysis apparatus. For example, a test may be made to determine the light absorption of a fluid or the time rate of change of light absorption due to a chemical reaction. Typically, light is passed to a detector through a cuvette holding the fluid to be tested. The absorbence of the fluid in the cuvette is measured and used to determine certain characteristics of the measured fluid.

In photoanalysis systems performing the above described tests the cuvettes used to hold the test fluid must be of relatively high optical quality. The light must pass through the cuvette without substantial absorption, reflection or refraction. This requirement dictates that the cuvettes be manufactured from a relatively high quality material.

In order to further enhance the refractive characteristics of the cuvette, certain cuvettes have been manufactured in a square or rectangular configuration. When this type of cuvette is placed in a photoanalysis apparatus the light passes through the parallel side walls in a direction perpendicular to the walls themselves. This minimizes the distortion, reflection and refractions of the incident light beam as it passes through the cuvette while the substantially parallel rays incident unto the cuvette remain parallel after passage through the cuvette.

In some photoanalysis methods and apparatus, because of the small quantity of fluid available for analysis, and because of the light transmission characteristics in the tests performed, it is advantageous to pass a light beam through the cuvette and sample more than once. The problems associated with such a technique are of course apparent. Passing the light beam through a cuvette more than once will act to exacerbate any optical distortion, refraction or reflection of the light beam produced by the cuvette itself and will further act to increase the optical absorption resulting from passage of light through the cuvette.

The square or rectangular cross section of the cuvette would appear to provide the best light transmitting characteristics. However, if the cuvette is reused in subsequent tests, such as is true in an automated system, the square or rectangular cross section is an undesirable configuration. This is because the right angle corners in the cuvette act to trap portions of the fluid and hold the fluid so that it will be carried over to the subsequent sample contaminating the subsequent sample and possibly adversely affecting the test. Furthermore, a square or rectangular cuvette provides little or no possibility of controlling the beam width passed to the detector or the beam refraction.

The lowest possible carryover obtainable results when the internal cross section of the cuvette, which carries the fluid to be analyzed, is circular. However, to make an optimum optical absorption measurement, the light rays must go through the sample fairly parallel to each other and as previously noted, this dictates that the cross section of the cuvette be either rectangular or square. The problem presented then is to resolve this basic conflict between optimum absorption measurement and minimum carryover.

In addition to the desirability of a low carryover, the cuvettes used must be easy to build and low in cost, thus eliminating the possibility of forming exotic surfaces by expensive grinding and polishing operations.

Lastly, in some instances it is desirable to somewhat focus or control the light beam received by the detector, but this can only be accomplished while maintaining the light rays in a nearly parallel direction.

SUMMARY OF THE INVENTION

In practicing this invention, a cuvette is supplied for containing a fluid to be analyzed by passage of light therethrough. The cuvette is adapted to be positioned at a predetermined distance from the optical elements in a light detection scheme. The cuvette comprises an elongate hollow, cylindrical structure. The cylinder is formed by a wall with a circular inner surface at a radius $a$ about the structural axis defining a compartment to contain the fluid to be analyzed. The outer surface is generally concentrically circular with respect to the structure's axis and has a radius $b$ with a flat portion formed on the outer surface extending in a plane parallel to the cylindrical axis and perpendicular to the optical axis of an associated light detector. The flat portion of the outer surface is positioned a predetermined radial distance $d$ from the structural axis.

DETAILED DESCRIPTION OF THE PREFERRED EMBODIMENT

Figures 1, 2, 3:
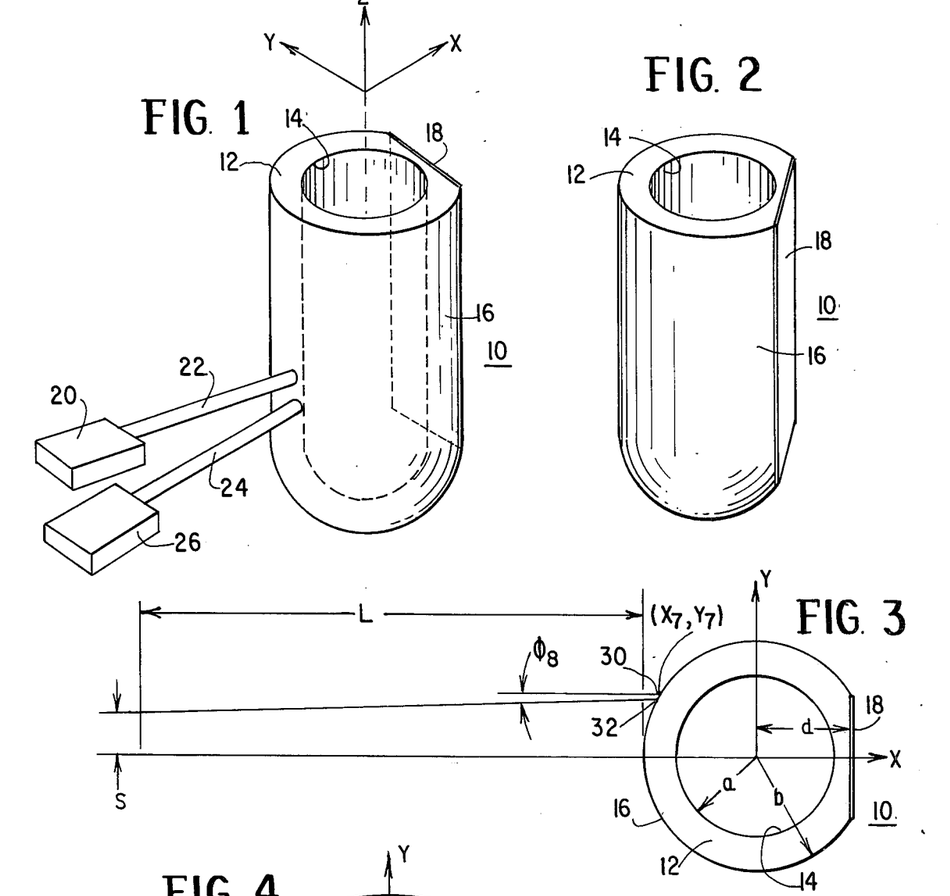
FIG. 1 is a perspective view of the cuvette of this invention.
FIG. 2 is another perspective view of the cuvette of this invention.
FIG. 3 is a top view of the cuvette of this invention showing a light ray passing to the cuvette.

Referring now to FIGS. 1 and 2, there is shown a cuvette 10 for containing a fluid to be analyzed by passage of light through the fluid. Cuvette 10 is in the form of a generally cylindrical structure. The cuvette is formed by a cylinder wall 12 which has a circular inner surface 14 that extends the full length of cuvette 10. Wall 12 and inner surface 14 define a cylindrical compartment which is closed at the bottom end, opened at the top end and holds the fluid to be analyzed. FIG. 1 shows an XYZ cartesian coordinate system above cuvette 10. The structural axis of cuvette 10 lies along the Z axis of the coordinate system. Surface 14 is located at a radius $a$ about the cylindrical axis of cuvette 10. The cuvette can be described as having a plane of symmetry lying along the XY axis of the cartesian XYZ coordinate system, as will be evident from FIGS. 3 and 4 as hereinafter described.

Wall 12 of cuvette 10 also has a circular outer surface 16 located at a radial distance $b$ from the structure axis. Surface 16 is circular for a substantial portion of the circumference of cuvette 10. However, a portion 18 of outer surface 16 is flat for a purpose to be more clearly explained subsequently. The flat portion lies in a plane that extends parallel to the Y-Z plane. Surface 18 is located at a distance $d$ from the Z axis of the coordinate system shown in FIG. 1.

When used in a photoanalysis apparatus, a light source and its associated optical elements 20, which may be, for example, a laser, develops a beam 22 of substantially parallel light rays and the beam is projected onto cuvette 10. In the embodiment shown, wall 12 of cuvette 10 is made from a low light asorbing material such as for example, glass, diamond, germanium, sapphire, magnesium floride, fused silica, plastic or quartz so that light beam 20 passes through wall 12 and through the fluid in the compartment formed therein and then again through wall 12. Flat surface 18 is mirrored, although it is to be understood that a mirrored surface is not necessary and that a mirror may be provided external to cuvette 10.

Light beam 22 strikes the mirrored surface 18 in the preferred embodiment substantially perpendicular to surface 18. That is, surface 18 extends parallel to the Y-Z plane shown in FIG. 1 and light beam 22 substantially lies in the X-Z plane of the coordinate system. Beam 22 is offset slightly from the center of the XYZ coordinate system, along the Z axis, so that it enters cuvette 10 at a slightly downward angle and is reflected slightly downward back through wall 12 and the fluid in the chamber in cuvette 10. The reflected light rays leave in a beam 24 and pass to a light detector 26.

The circular configuration of inner surface 14 forming a cylindrical compartment in cuvette 10 for holding the fluid to be analyzed, results in a configuration, which minimizes sample carryover of sample serially injected into cuvette 10. The plano-convex outer configuration of cuvette 10, which when viewed in cross section appears as a D shape, results in each exiting ray of light in beam 24 being substantially parallel to each entering ray of light in beam 22 through the fluid in cuvette 10. This means that similar to the square or rectangular configured cross section, this cuvette has afocal properties. This characteristic is based on the focusing properties of the air-wall liquid interfaces acting on the incoming rays of beam 22 (points 1 and 2 of FIG. 4). The focusing effects are balanced by the diverging properties of the fluid-wall-flat surface interfaces (points 3 and 4 of FIG. 4) acting on the outgoing rays. The specific configuration is then equivalent to an optical configuration oftentimes known as a "Cook's triplet". If the entering and exiting rays in beams 22 and 24 are substantially parallel to one another through cuvette 10, the interference with the photoanalysis measurements will be minimized.

It must be remembered that light beams 22 and 24 pass through an environment, or medium between source 20, cuvette 10 and detector 26. Generally the environment will be air; however, the cuvette could be employed in a vacuum or a liquid or an inert atmosphere or a solid, such as fiber optics. The index of refraction for the environment will be defined as $n_1$, although the index of refraction for any specific environment such as air has a specific value. the light beams also pass through wall 12. Wall 12, as previously noted, can be glass, plastic or quartz depending upon the material and composition used, can have any index of refraction larger than the surrounding environment and larger than the fluid. The index of refraction for wall 12 will be defined as $n_2$. The fluid contained within cuvette 10 will be analyzed also will have a specific index of refraction which will be defined as $n_3$.

Although the configuration shown for cuvette 10 yields light beams 20 and 22 whose rays are substantially parallel within the cuvette, they are not exactly parallel. The degree of uniformity between the incoming and exiting rays is determined to a substantial degree by the index of refraction of the media through which the light beams travel and the various dimensions for cuvette 10.

A hollow cylindrical structure defining a compartment is necessary as previously noted in order to assure minimum carryover but as also previously noted, this structure does not produce entering and exiting rays of light through the cuvette which are close to being parallel to one another. The plano-convex configuration shown in FIGS. 1 and 2 which appears as a "D" in cross section results in parameters for the cuvette which can be varied with respect to one another so as to provide maximum control over the light beam exiting the cuvette while still providing the closest possible parallel relationship between the incoming and exiting rays of light within the cuvette. This control is important in many apparatus configurations.

In certain apparatus it is desirable to employ the smallest possible photodetector 26. Physical restraints dictate that the detector 26 and more specifically, the field-stop therein, be located at a specified distance L from the closest facing surface 16 of cuvette 10. In such an environment, it is desirable to select the cuvette parameters so that all of the exiting light rays strike the detector 26 and are received by the optical elements therein, while of course maximizing the parallel nature of the light rays through the cuvette.

Figure 4:
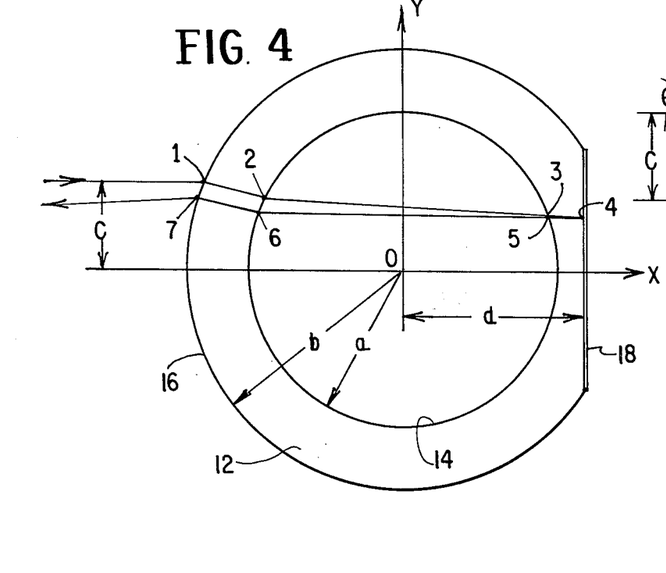
FIG. 4 is a top view of the cuvette of this invention showing the tracing of a light ray through the cuvette at each of seven interfaces.

Referring now to FIGS. 3 and 4, a top view of cuvette 10 is shown with an X-Y coordinate system superimposed over the cuvette. FIG. 1 shows light beam 22 and light beam 24 at different heights. For purposes of simplicity in this analysis we assume they enter and exit at the same height. That is, we make the assumption that we are dealing with a two-dimensional rather than a three-dimensional system and perform all necessary computations for the two dimensional system. Performing the much more complicated analysis in three dimensions changes the results less than a negligible amount since any spreading of the rays substantially takes place in the X-Y plane.

A light ray in beam 22 farthest from the optical axis is substantially parallel to the optical axis and strikes and enters cuvette 10 at a point 30, also identified in FIG. 4 by the number 1 and the coordinates $(X_1,Y_1)$ with respect to the X-Y coordinate axis. This entering ray passes through cuvette 10 and through the fluid therein and is reflected from mirrored flat surface 18 back through the fluid to be analyzed in cuvette 10 exiting cuvette 10 at location 32 identified in FIG. 4 by the number 7 and by the coordinate $(X_7,Y_7)$ in FIG. 3. The light ray exits at an angle $\phi_8$ with respect to the optical axis and passes to detector 26 located at a distance L from the front surface 16 of cuvette 10. The maximum distance from the optical axis of an exiting light ray in beam 24 at a distance L from cuvette 10 is represented in FIG. 3 by a symbol S.

In order to determine S, the following trigonometric equation is solved:

$$S = Y_7 - (L + b + X_7)(\tan \phi_8) \quad (1)$$
$$(X_7 \text{ less than } 0)$$

In order to determine $X_7$ and $Y_7$ the light ray must be traced as it progresses through the cuvette 10. Referring to FIG. 4 the light ray enters from the left at a distance c from the optical axis of the incident beam. The light ray strikes outer surface 16 of cuvette 10 at point 1 and proceeds through wall 12 exiting the cuvette and entering the fluid in the cuvette at point 2. From point 2 the light passes through the fluid in cuvette 10 and strikes wall 12 at point 3 entering the wall and striking mirrored flat surface 18 at point 4. At point 4 the light ray is reflected from the mirrored surface again passing through wall 12, exiting wall 12 and entering the fluid at location 5. The reflected ray now passes through the fluid in cuvette 10 and enters wall 12 at location 6. From location 6 the ray proceeds through wall 12 exiting cuvette 10 at point 7.

Here, as an example, a ray is traced with two passes through the cuvette with a mirror on the surface 18. For one skilled in the art, it is possible to trace a ray through the cuvette with one or more passes of the light beam (with the mirror on or not on surface 18), using this formalism. It is to be understood the effects on the parallel nature of rays in a light beam of even a single pass of the beam through cuvette 10 are minimized by the plano-convex configuration.

The subscripts in the following equations refer to the point number (1 through 7), (X,Y) to the X-Y coordinates, and $(\theta,\theta')$ to the ray angle entering and leaving the point, respectively.

Figure 5:
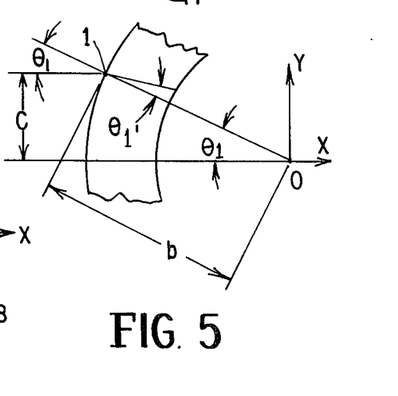
FIG. 5 shows a portion of the cuvette at interface point 1 showing the angles and locations necessary for certain trigonometric calculations.

From FIG. 5:

$$X_1 = \sqrt{b^2 - c^2}; Y_1 = c \quad (2)$$

$$\theta_1 = \arcsin\left(\frac{c}{b}\right) \quad (3)$$

$$\sin \theta'_1 = \frac{n_1 c}{n_2 b} \text{ (Snell's law)} \quad (4)$$

$$\theta'_1 = \arcsin \frac{n_1 c}{n_2 b} \quad (5)$$

Figure 6:
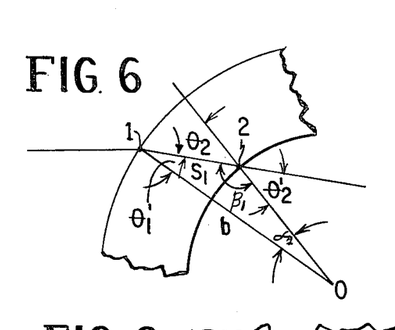
FIG. 6 is a top view of a portion of the cuvette at interface point 2 showing angles and locations necessary for certain trigonometric calculations.

Passing now to FIG. 6 depicting point 2 and the necessary analysis thereof, from the law of sines:

$$\frac{b}{\sin \beta_1} = \frac{s_1}{\sin \alpha_1} = \frac{a}{\sin \theta'_1} \quad (6)$$

After performing certain trigonometric manipulations, $$\theta_2 = \text{Arcsin} (\sin\theta'_1 \times [b/a]) \text{ and} \quad (7)$$

$$\theta'_2 = \text{Arcsin} (n_2 \sin\theta_2/n_3) \quad (8)$$

Figure 7:
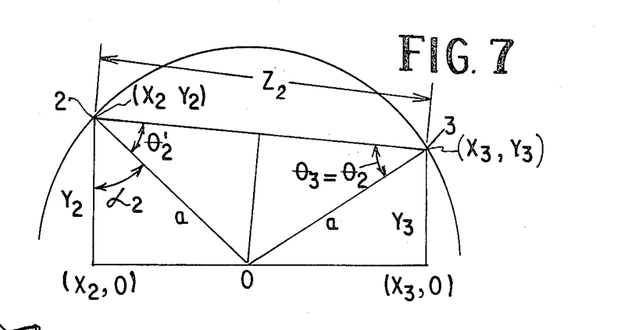
FIG. 7 is a top view of a portion of the cuvette at interface point 3 showing angles and locations necessary for certain trigonometric calculations.

Moving now to point 3, FIG. 7 shows the triangles, angles and lengths necessary to determine the coordinates of point 3. Performing the necessary trigonometric manipulations:

$$\theta_3 = \theta'_2 \quad (9)$$

$$\theta'_3 = \theta_2 \quad (10)$$

$$X_3 = X_2 + Z_2 \sin(\alpha_2 + \theta'_2) \quad (11)$$

$$Y_3 = Y_2 - Z_2 \cos(\alpha_2 + \theta'_2) \quad (12)$$

where $\alpha_2 = \text{Arctan}(-X_2/Y_2)$; $Z_2 = 2a\cos\theta'_2$

Figures 8, 9:
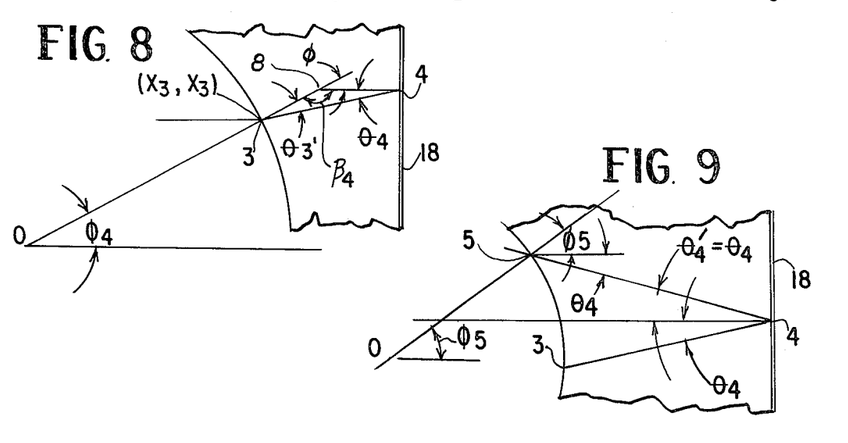
FIG. 8 is a top view of a portion of the cuvette at interface point 4 showing angles and locations necessary for certain trigonometric calculations.
FIG. 9 is a top view of a portion of the cuvette at interface point 5 showing angles and locations necessary for certain trigonometric calculations.

Moving now to FIG. 8, this shows the necessary relationships to determine the coordinates at point 4. It is known that $X_4 = +d$. In order to determine $Y_4$, we consider the triangle 3, 4 and 8. Performing the necessary trigonometric manipulations, we obtain $$Y_4 = Y_3 + (d - X_3) \tan \theta_4 \quad (13)$$

$$\theta_4 = \text{Arctan}(Y_3/X_3) - \theta_2 \quad (14)$$

$$\theta'_4 = \theta_4 \quad (15)$$

Moving now to point 5, FIG. 9 shows the triangle formed by points 3, 4 and 5 and the various relationships therebetween for determining the coordinates at point 5. Performing the necessary trigonometric manipulations and using the quadradic formula yields the formulas $$X_5 = -\frac{A_2 + \sqrt{A_2^2 - 4A_1A_3}}{2A_1} \quad (16)$$

where
$A_1 = 1 + \tan^2\theta_4$
$A_2 = -2X_4 \tan^2\theta_4 = 2Y_4 \tan \theta_4$
$A_3 = -a^2 + Y_4^2 + X_4^2 \tan^2\theta_4 + 2Y_4X_4 \tan \theta_4$ $$Y_5 = \sqrt{a^2 - X_5^2}$$

Equations 16 and 17 are solved simultaneously yielding $$\theta_5 = \text{Arctan}(Y_5/X_5) + \theta_4 \quad (18)$$

By use of Snell's law we obtain
$$\theta'_5 = \text{Arcsin}(n_2 \sin\theta_5/n_3) \quad (19)$$

Figures 10, 11:
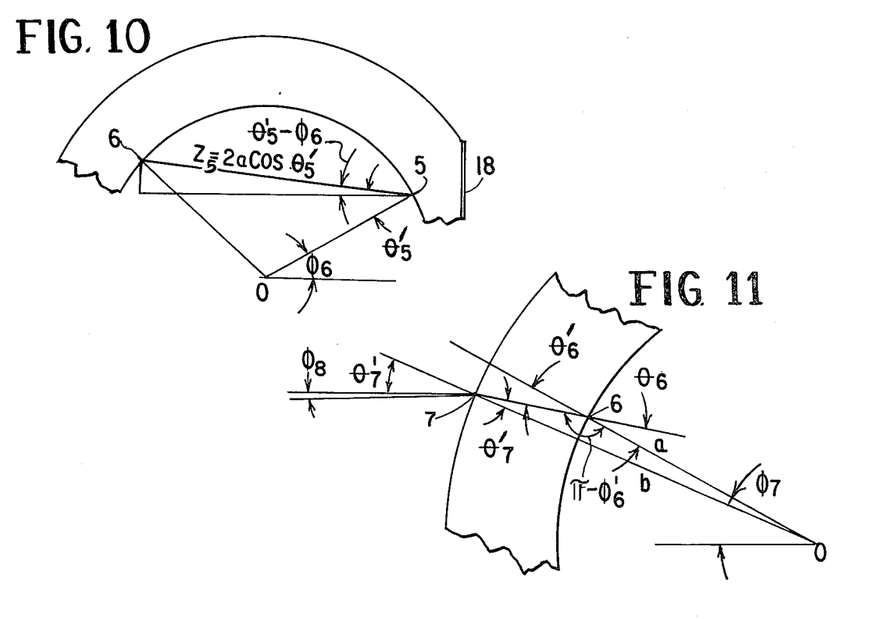
FIG. 10 is a top view of a portion of the cuvette of this invention at interface point 6 showing angles and locations necessary for certain trigonometric calculations.
FIG. 11 is a top view of a portion of the cuvette at interface point 7 showing angles and locations necessary for certain trigonometric calculations.

Moving now to FIG. 10, this correlates point 6 in cuvette 10 with point 5 and with the center of the coordinate system. Performing the necesary trigonometric manipulations to determine $X_6$, $Y_6$ and $\theta_6$, we obtain $$X_6 = X_5 - Z_5 \cos(\theta'_5 - \theta_6) \quad (20)$$

$$Y_6 = Y_5 Z_5 \sin(\theta'_5 - \theta_6) \quad (21)$$

$$\theta_6 = \theta'_5; \theta'_6 = \theta_5 \quad (22)$$

where $Z_5 = 2a'_5$; $\phi_6 = \text{Arctan}(Y_5/X_5)$

Moving now to FIG. 11, this shows the relationships between points 6 and 7 and the center of the coordinate system. Considering the triangle formed by the points 6, 7 and the center of the coordinate system and performing the necessary trigonometric manipulations, we obtain $$\theta_7 = \text{Arcsin}([a/b] \sin \theta_5) \quad (23)$$

$$X_7 = -b\cos\phi_7 \quad (24)$$

$$Y_7 = b \sin\phi_7 \quad (25)$$

where $\phi_7 = \text{Arctan}(-Y_6/X_6) - \theta'_6 + \theta_7$ $\phi_8$ is the angle the exiting ray makes with the horizontal. $\phi_8$ then is $$\phi_8 = \text{Arctan}(-Y_7/X_7) - \theta'_7 \quad (26)$$

$$\theta'_7 = \text{Arcsin}(n_2 \sin\theta_7/n_1) \quad (27)$$

By use of the above calculations, one can fully determine the geometry of an exiting ray and, by selection of the various parameters such as $n_1$, $n_2$, $n_3$, $a$, $b$, $c$ and $d$ one can determine the maximum distance S from the optical axis at a distance L from the cuvette 10 of a ray of light exiting cuvette 10.

Assume one wishes to place detector 26 at a specified distance L from a cuvette. Assume further that the three indices of refraction are specified to have certain values, because the material of cuvette 10 will be known, the index of refraction for the fluid to be analyzed will be determinable and should be constant and of course, the index of refraction of the environmental material between the cuvette and the detector is also known and constant. Because standard size cuvettes are generally used with the light path traveling through a predetermined path line of fluid, the inner diameter 2a of the cuvette can also be considered to be specified. With the above noted parameters specified, the only parameters which have not been specified are c, the distance from the optical axis at which a ray of entering light in light beam 22 enters cuvette 10, and b the radius to outer surface 16 of cuvette 10.

These values can be selected to suit the users' needs for a particular cuvette and beam size, for example to fit into a particular holder. However, by appropriate selection of values for c and b, it is possible to minimize the distance S from the optical axis of the exciting beam at a distance L from the cuvette, of an exiting ray of light in beam 24 where the entering ray which resulted in the exiting ray entered cuvette 10 at location c. This process for minimizing this maximum distance is known as an interaction process and it is performed as follows.

Figure 12:
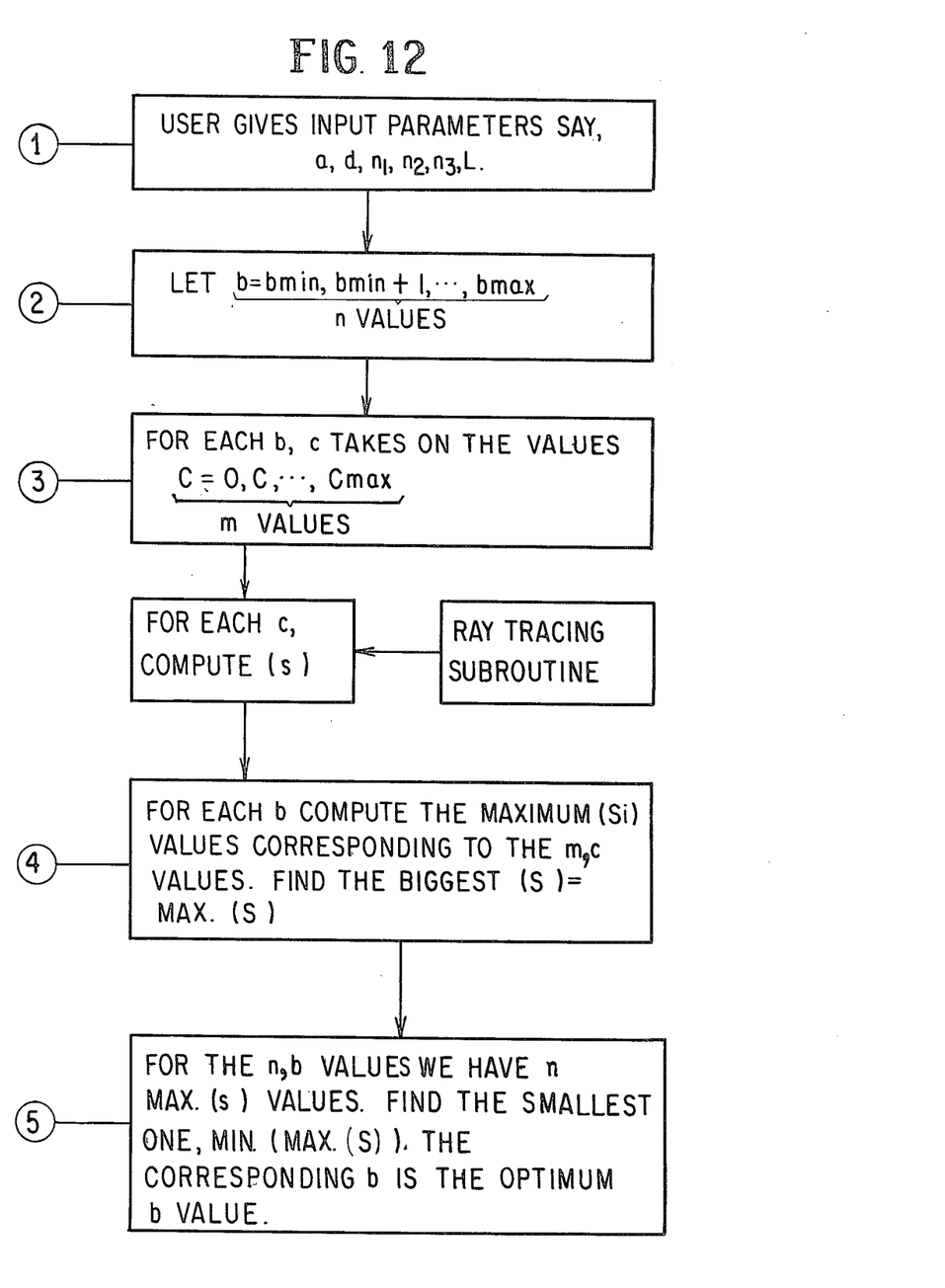
FIG. 12 is a flow chart of the iteration process described for ascertaining S.

Select a range of possible values for b and a range of possible values for c. The range of values for c extends from 0 to some maximum distance from the optical axis defined as $c_{max}$. Select a number of specific values for c within the specified range. Then select one value of b within the specified range and with that one value of b calculate S for each value of c selected. Determine which value of c for the selected b yields a maximum S and retain that maximum S and the associated c and b. Then select another value of b and again calculate S for each value of c within the range of 0 to $c_{max}$. Again ascertain which value of c with the selected value of b yields a maximum S and store the maximum S and the c and b values used to obtain the maximum S. Continue the above noted procedure for each value of b selected within the range of values. When all selected values of b have been utilized, find the value for minimum maximum S. This value will be the maximum distance from the optical axis of an exiting light ray which enters cuvette 10 at a point c parallel to the optical axis, so that a detector located a distance L from cuvette 10 must have a radius slightly larger than the determined S when a cuvette is utilized having the parameters initially selected and the parameters for b and c corresponding to the noted S. A flow chart of the iteration process is shown in FIG. 12.

The above example represents the situation where the cuvette parameters are selected in order to minimize the distance of an exiting ray from the optical axis at a distance L from the cuvette 10 when the entering ray enters at a distance c from the optical axis. In some cases, it may be more desirable to make the entering and exiting rays perfectly parallel. If this is the case, then L is selected to be very large, for example, 10 meters while a and b are in the range of 0.01 meters and b and c varied as noted above to select S. Alternately, S can be specified to be equal to c at a distance L and c can be varied to ascertain preferred values of b and/or d.

While the present invention has been described by reference to a specific example, it is to be understood that modifications may be made by those skilled in the art without actually departing from the invention shown and described herein. It is therefore intended that the appended claims cover all variations that fall within the scope and spirit of this invention.

What is claimed and desired to be secured and claimed by Letters Patent of the United States is:

1. An afocal cuvette for containing a fluid to be analyzed by passage of light therethrough, said cuvette adapted to be positioned at a predetermined distance L from a light receptor, said cuvette comprising:

a hollow cylindrical structure having a structural axis and an axis of symmetry defined by an XYZ cartesian coordinate system wherein the structural axis lies along the Z axis and the plane of symmetry lies along the XY axis, said cylindrical structure having a circular wall and a flat portion formed on the exterior surface of said circular wall extending in a plane parallel to the structural axis, at least said circular wall being optically transparent, said circular wall having a circular inner surface at a radius a about the structural axis for defining a compartment to contain the fluid and a circulr outer surface having a radius b, said flat portion being positioned a predetermined radial distance d from said structural axis, said cuvette capable of receiving incident light along an incident light path defined as an incident beam formed of a plurality of rays from a light source which is located at a distance spaced from the cuvette and the beam having a first optical axis, the beam continuing through said cuvette wall and the compartment to the said flat portion and at least a portion of the beam being reflected back from said first portion as a reflected beam also formed as a plurality of reflected rays, the beam having a second optical axis and lying along an exiting light path defined as leading to the light receptor which is located spaced offset from the optical axis of the incident light beam and from the light source, the first and second optical axes being on opposite sides of said plane of symmetry, the indices of refraction of the media intercepted by said incident and exiting light beams being related to said radii and predetermined distance whereby to effect definition of the rays forming said incident and exiting light beams into and out from said cuvette as substantially parallel within their respective beams.

2. The cuvette of claim 1 wherein said incident light path enters said cuvette through said circular wall.

3. The cuvette of claim 1 wherein said wall is formed from one of the materials, glass, plastic, germanium, sapphire, magnesium fluoride, quartz and fused silica.

4. The cuvette of claim 1 wherein said flat portion has a mirrored surface applied thereto.

5. The cuvette of claim 1 and in combination a light source for transmitting incident light to said cuvette, said incident light beam reaching said cuvette at a maximum distance $c$ offset from the X axis with respect to the XY plane of symmetry; said light receptor being centered on the second optical axis, and having a receptor surface of sufficient size to receive substantially all the rays forming the reflected beam which will deviate a maximum distance S from said second optical axis, the media through which said incident and reflected light pass including a medium exterior of said cuvette having an index of refraction $n_1$, the medium forming said cuvette having an index of refraction $n_2$ and said fluid interior of said compartment having an index of refraction $n_3$; said values of $a$, $b$, $c$, $d$, and $n_1$, $n_2$ and $n_3$ being selected so that said maximum distance S is defined by the equation $S = Y_7 - (L + b - X_7)(\tan \phi_8)$ where $X_7$ and $Y_7$ are the X,Y coordinates of the point at which the reflected light exits the circular outer surface of the cuvette with the center of the coordinate system being at the structural axis of the cuvette and the X direction being along the X axis of the XY plane of symmetry, the angle $\phi_8$ being the angle at which the optical axis of the exiting beam makes relative to the optical axis of the incident beam.

6. The cuvette of claim 5 wherein at least a first and second of the parameters $a$, $b$, $c$, $d$, $n_1$, $n_2$, $n_3$ or L, have a number of different values with the remaining parameters assigned predetermined values, the maximum S being determined for the number of different values of the first parameter with one of the second parameters, then with each other one of the different values of the second parameter and the minimum one of the determined maximum S values being selected as the maximum distance.

7. The cuvette of claim 5 wherein $n_2$ is larger than $n_1$ and $n_3$.

8. The cuvette of claim 6 wherein $n_2$ is larger than $n_1$ and $n_3$.

9. The cuvette of claim 6 wherein $n_2$, the index of refraction for the cuvette material, is selected from the range of values of 1.01 to 2.70.

10. The cuvette of claim 6 wherein said flat surface has a mirrored surface applied thereto.

11. The cuvette of claim 1 and a light source transmits incident light to said cuvette, said incident light is reflected back at least a first time, said incident light and reflected light passing through a medium having an index of refraction $n_1$ to and from said structure, said cuvette having an index of refraction $n_2$ and said fluid having an index of refraction $n_3$, said values $a$, $b$, $d$, $n_1$, $n_2$ and $n_3$ being selected so that the parallelism of said incident and reflected light paths passing through said fluid is maximized and the light receptor location is defined by the equation $S = Y_7 - (L + b + X_7)(\tan \phi_8)$ where S is the maximum distance the reflected beam will deviate from the second optical axis the light receptor being centered on the second optical axis, $X_7$ and $Y_7$ are the X, Y coordinates of the point at which the reflected light exits the circular outer surface of the cuvette with the center of the coordinate system being at the structure axis and the X direction being along the XY plane of symmetry, said value of L being great as compared to S and $b$.

12. A method for locating the position of a light receptor relative to a cuvette to enable receipt of the maximum reflected light wherein incident light ray is transmitted with respect to a first optical axis through the cuvette which is positioned a distance L from the light receptor and reflected back through said cuvette and to said receptor with respect to a second optical axis, the said cuvette being a hollow cylindrical structure having a wall and a circular inner surface at a radius $a$ about a structural axis, a circular outer surface having a radius $b$, said outer surface having a flat portion formed thereon extending in a plane parallel to the structural axis and perpendicular to an XY plane of symmetry taken through the cuvette normal to the structural axis thereof, said flat portion positioned at a predetermined distance $d$ from the structural axis, said incident light ray reaching said cuvette at a maximum distance $c$ from the optical axis and said light receptor being centered on the second optical axis and located so that light in the reflected beam will deviate a maximum distance S from the second optical axis, in order that substantially all the reflected light would reach the receptor, said incident and reflected light passing through a medium having an index of refraction $n_1$, the cuvette having an index of refraction $n_2$ and the fluid therein having a refraction index $n_3$, said method comprising the steps of:

(a) selecting a number of different values for at least a first and a second of the parameters $a$, $b$, $c$, $d$, $n_1$, $n_2$, $n_3$ or L;

(b) assigning predetermined values to the remaining parameters;

(c) determining S for the number of different first parameters with a particular one the number of second parameters;

(d) storing the maximum S from among those determined in (c) and the corresponding first and second parameters;

(e) repeating (a) and (d) for each different one of the number of second parameters; and (f) locating the receptor at the distance offset representing the smallest S of those stored values with the cuvette constructed in accord with the values of the first and second parameters which yield said smallest S.

13. The method of claim 12 wherein the S selected is defined by the equation $S = Y_7 - (L + b + X_7)(\tan \phi_8)$ where $X_7$ and $Y_7$ are the X,Y coordinates of an XYZ cartisian coordinate system of the point at which the reflected light exits the circular outer surface of the cuvette with the center of the coordinate system being at the structural axis of the cuvette and the X direction being along the XY plane of summetry of the cuvette and the angle $\phi_8$ is the angle defined by the incident and reflected light rays at the point represented by $X_7Y_7$.

14. An afocal cuvette for containing a fluid to be analyzed by passage of light therethrough, said cuvette comprising: a hollow cylindrical structure having an optically transparent wall with a circular inner surface at a radius $a$ about the structural axis of the cuvette for defining a compartment for containing said fluid and a plano-convex outer surface having a circular outer portion at a radius $b$ about the structure axis and a flat reflective portion at a distance $d$ from the structural axis of said cuvette, the media through which the light passes having indices of refraction and said indices, said radii and said distance $d$ being selected to assure maximum parallelism of the rays within the incident and exiting light beams passing through the cuvette.

15. The cuvette of claim 14 wherein media through which the light passes includes an atmosphere exterior of the cuvette which has an index of refraction $n_1$, the cuvette wall has an index of refraction $n_2$ and the index of refraction of the cuvette wall is substantially greater than the indices of refraction of the fluid in the compartment and/or the surrounding environmental medium.

* * * * *

UNITED STATES PATENT AND TRADEMARK OFFICE
CERTIFICATE OF CORRECTION

PATENT NO. : 4,115,011
DATED : September 19, 1978
INVENTOR(S) : ALBERT BRUNSTING It is certified that error appears in the above-identified patent and that said Letters Patent are hereby corrected as shown below:

Column 3, line 62, Insert hyphen between "wall" and "liquid;
Column 4, line 13, "the should be --The--;
Column 4, line 19, After "10" change "will" to --to--;
Column 6, line 22, "$X_4$" should be in italics;
Column 6, line 22, "$Y_4$" should be in italics;
Column 6, line 40, The minus sign should be in front of "$A_2$" rather than the entire equation;

Column 6, line 44, Change second occurrence of "=" to a minus sign
Column 6, line 63, "$\theta_6$" should be --$\phi_6$--;
Column 6, line 64, "$\theta_6$" should be --$\phi_6$--;
Column 6, line 66, After "a" insert --cos θ--;
Column 8, line 48; "circulr" should be --circular--;

Signed and Sealed this

Eighteenth Day of September 1979

[SEAL]

Attest:

Attesting Officer

LUTRELLE F. PARKER
*Acting Commissioner of Patents and Trademarks*